US008032123B2

(12) United States Patent
Sakhpara

(10) Patent No.: US 8,032,123 B2
(45) Date of Patent: Oct. 4, 2011

(54) MOBILE HANDSET WITH AIR POLLUTION METER AND SYSTEM

(75) Inventor: Ketul Sakhpara, Plano, TX (US)

(73) Assignee: Samsung Electronics Co., Ltd., Suwon-si (KR)

( * ) Notice: Subject to any disclaimer, the term of this patent is extended or adjusted under 35 U.S.C. 154(b) by 1220 days.

(21) Appl. No.: 11/465,989

(22) Filed: Aug. 21, 2006

(65) Prior Publication Data

US 2008/0045156 A1  Feb. 21, 2008

(51) Int. Cl.
*H04M 3/42* (2006.01)
(52) U.S. Cl. .......... 455/414.1; 455/412.1; 455/423; 455/66.1
(58) Field of Classification Search ........... 455/414.1, 455/412.1, 423, 66.1
See application file for complete search history.

(56) References Cited

U.S. PATENT DOCUMENTS

| 6,166,627 | A   | * | 12/2000 | Reeley ............... 340/426.25 |
|-----------|-----|---|---------|----------------------------------|
| 6,703,930 | B2  | * | 3/2004  | Skinner ............... 340/539.11 |
| 7,019,652 | B2  | * | 3/2006  | Richardson ............ 340/573.1 |
| 7,378,954 | B2  | * | 5/2008  | Wendt ................ 340/539.11 |
| 2006/0141945 | A1 | * | 6/2006 | Korhonen et al. ......... 455/90.1 |
| 2007/0109119 | A1 | * | 5/2007 | Zhang et al. .......... 340/539.22 |
| 2007/0241261 | A1 | * | 10/2007 | Wendt ................... 250/221 |

OTHER PUBLICATIONS

Margetta, Rob, CQ Staff, CQ Homeland Security—Technology, DHS Wants Cell Phones to Detect Chemical, Radioactive Material; http://public.cq.com/docs/hs/hsnews110-000002524221.html; Jun. 4, 2007; 9 pgs.

* cited by examiner

*Primary Examiner* — Yuwen Pan

(57) ABSTRACT

A mobile telecommunications handset is provided. The mobile telecommunications handset includes a component operable to measure a level of an air pollutant and a transceiver operable for a user to send and receive communications wirelessly.

20 Claims, 6 Drawing Sheets

Fig. 5
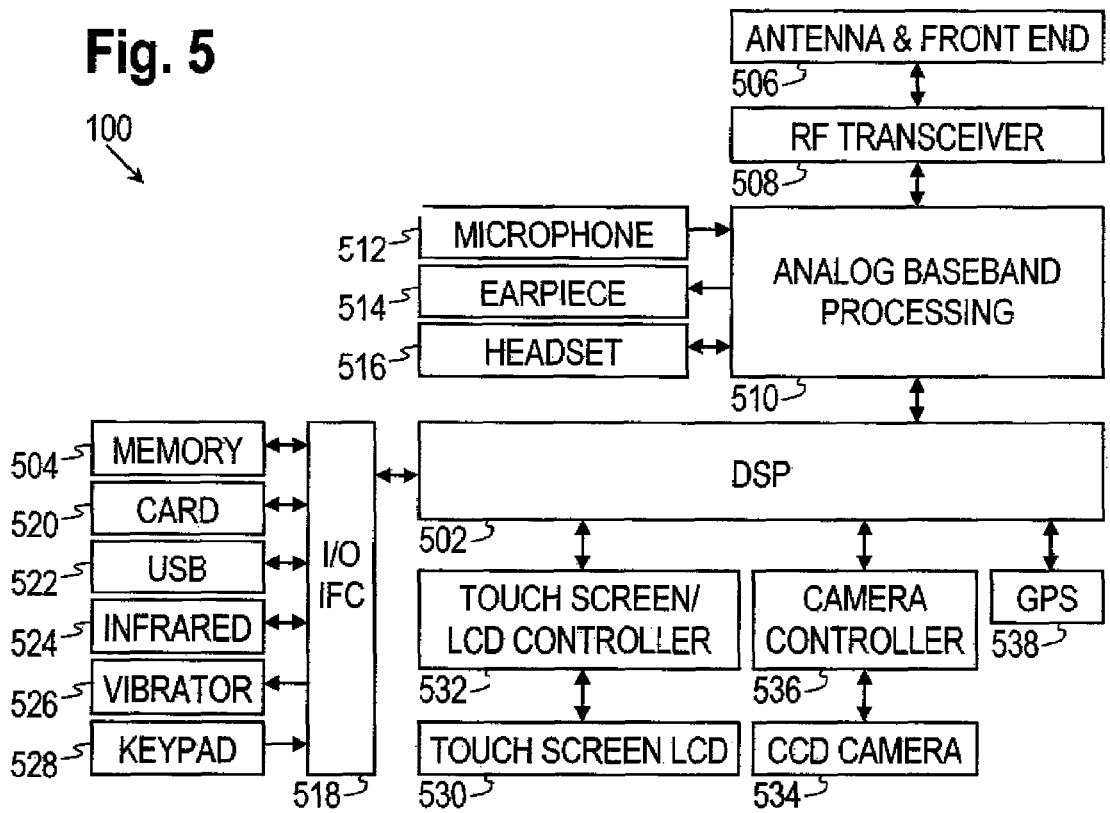
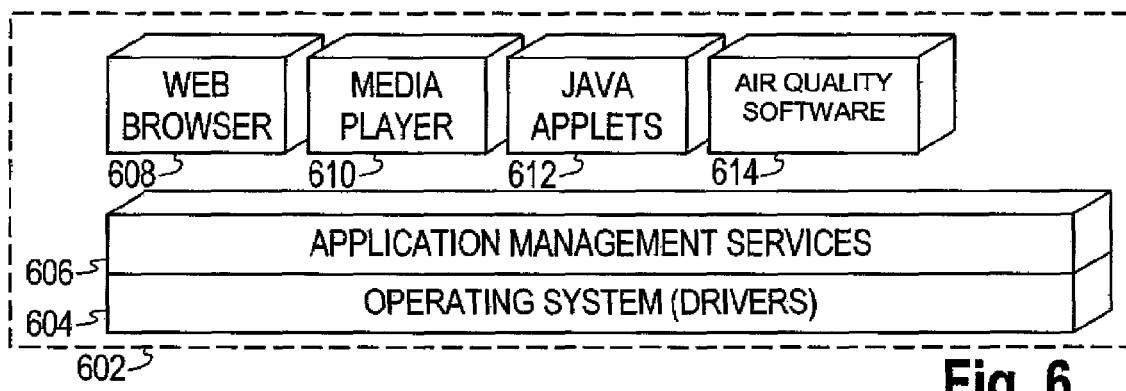
Fig. 6

MOBILE HANDSET WITH AIR POLLUTION METER AND SYSTEM

CROSS-REFERENCE TO RELATED APPLICATIONS

None

STATEMENT REGARDING FEDERALLY SPONSORED RESEARCH OR DEVELOPMENT

Not applicable.

REFERENCE TO A MICROFICHE APPENDIX

Not applicable.

BACKGROUND

Pollutants such as carbon monoxide, ozone, particulate matter, and other potentially harmful substances can be present in both indoor and outdoor air. Some cities and other municipal entities maintain air quality monitors to detect pollution levels. Reports of the air pollution levels measured by such monitors might be published in newspapers or on web sites, broadcast on television or radio, or otherwise be made known to the public. However, the monitors are typically present in only a limited number of locations and the air pollution levels measured in these locations do not necessarily represent the levels in other locations. Also, there may be some delay between the detection of an air pollutant and the announcement of the level of that pollutant. Changes could occur in a pollution level between the time a pollutant is detected and the time the level of that pollutant is published. Therefore, the pollution level a person is exposed to at a particular place and time could be significantly different from the published reports of air pollution levels.

SUMMARY

In one embodiment, a mobile telecommunications handset is provided. The mobile telecommunications handset comprises a component operable to measure a level of an air pollutant and a transceiver operable for a user to send and receive communications wirelessly.

In another embodiment, a system for recording a plurality of levels of an air pollutant at a plurality of locations is provided. The system includes a plurality of handsets, a component operable to promote determining the locations of the plurality of handsets, and a receiving device. The plurality of handsets are operable to measure the plurality of levels of the air pollutant and to transmit data related to the levels of the air pollutant and the locations. The receiving device is operable to receive the data related to the levels of air pollutants and the locations and use the data to create a record of the levels of the air pollutant at the plurality of locations.

In another embodiment, a method for measuring air pollution at a plurality of locations is provided. The method includes measuring air pollution using a plurality of mobile handsets, determining the locations at which at least some levels of the air pollution were measured, transmitting data related to the levels of air pollution at the locations, and using the data to create a record of the levels of air pollution at the locations.

These and other features and advantages will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIG. 5 is a block diagram of a handset operable for some of the various embodiments of the present disclosure.

FIG. 6 is a diagram of a software environment that may be implemented on a handset operable for some of the various embodiments of the present disclosure.

DETAILED DESCRIPTION

It should be understood at the outset that although an illustrative implementation of one embodiment of the present disclosure is illustrated below, the present system may be implemented using any number of techniques, whether currently known or in existence. The present disclosure should in no way be limited to the illustrative implementations, drawings, and techniques illustrated below, including the exemplary design and implementation illustrated and described herein, but may be modified within the scope of the appended claims along with their full scope of equivalents.

In an embodiment, an air quality sensor is included in a portable, wireless, handheld, electronic, consumer device such as a mobile telephone, a personal digital assistant, a handheld computer, or a similar device. Such devices will be referred to herein as handsets. The air quality sensor might detect levels of a single air pollutant or of multiple pollutants. Data collected by the air quality sensor might be transmitted to the central processing unit of the handset. The central processing unit might then cause a report of the pollutant levels to be displayed on the graphical user interface of the handset.

Alternatively or additionally, the handset might include a transceiver operable for cellular, digital, or other wireless communications and might wirelessly transmit the pollutant level data using well-known telecommunications protocols and/or well-known data transmission techniques for wireless computing networks. A central server or similar computing device might receive the pollutant level data transmitted by one or more handsets. The server might make data collected from a particular handset available to other handsets or other computing devices. For example, a pollution level detected by a child's handset might be transmitted from the child's handset to the server and from the server to a parent's handset or to the parent's fixed-location computer. Alternatively, the server might aggregate data collected from multiple handsets and create a map or other graphical depiction of the air pollution levels at multiple locations at a particular time. The map might be transmitted to handset users, published on the Internet, or otherwise be made available to interested parties.

Figure 1:
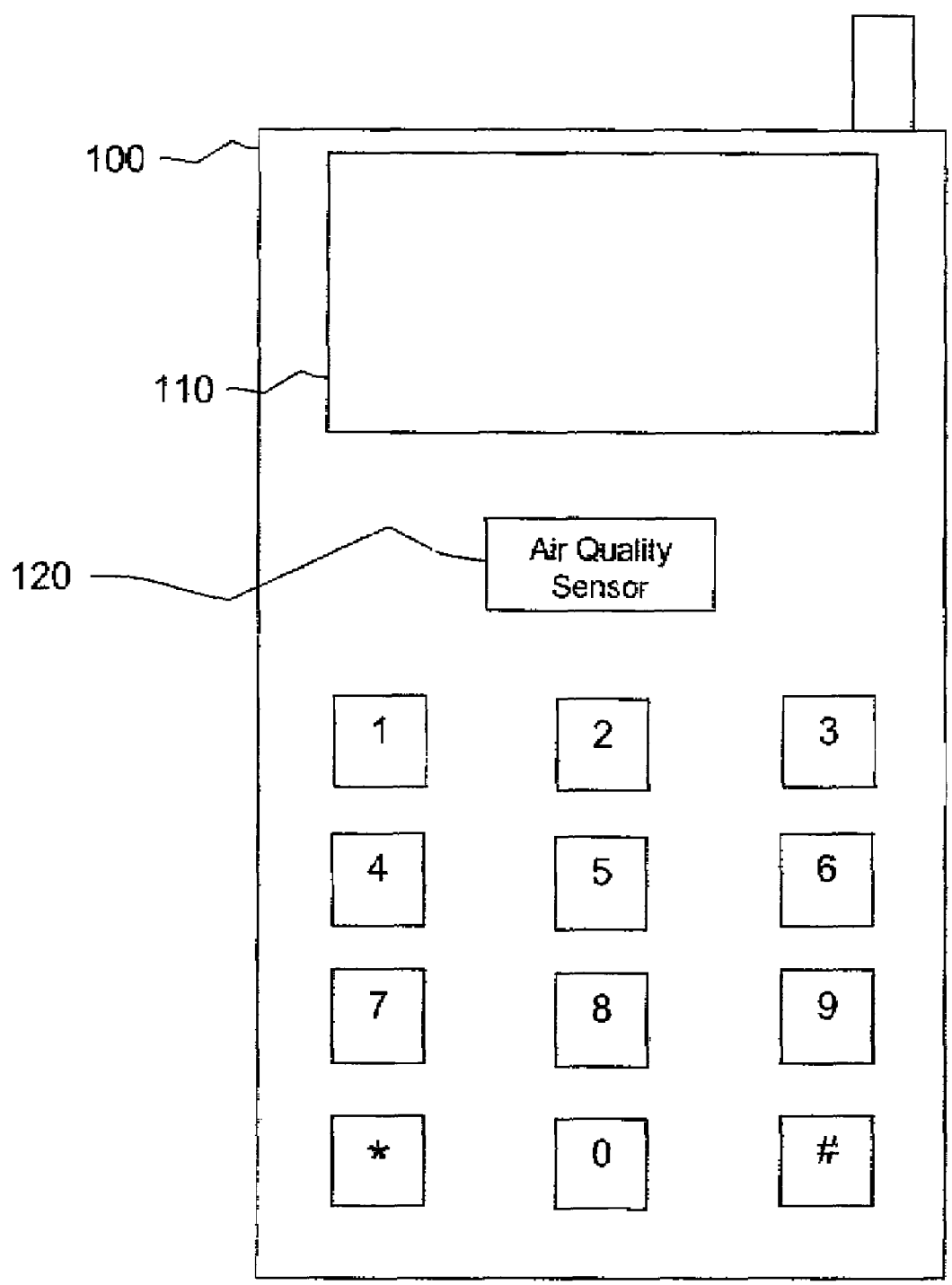
FIG. 1 illustrates a handset according to an embodiment of the disclosure.

FIG. 1 illustrates a handset 100 operable for the various embodiments of the present disclosure. The handset 100 includes a graphical user interface 110 operable to display data. The handset 100 also includes an air quality sensor 120 operable to measure the level of one or more air pollutants. While the air quality sensor 120 is depicted on the front portion of the handset 100 in FIG. 1, in other embodiments the air quality sensor 120 could be in other locations. Also, while the air quality sensor 120 is depicted in FIG. 1 as a single unit, in other embodiments the air quality sensor 120 could consist of multiple components.

The air quality sensor 120 might be capable of measuring the level of a single pollutant, such as carbon monoxide or ozone or any other aspect of air quality of interest and well known to those skilled in the art, or might be capable of measuring the levels of multiple pollutants. In an embodiment, air pollution level data collected by the air quality sensor 120 is transmitted to a central processing unit, digital signal processor, or similar controller in the handset 100. The central processing unit might then cause a report of the air pollution level data to be displayed on the graphical user interface 110. The data display might include a numerical report of the levels of each pollutant detected and/or an easily interpreted graphical display of pollutant level information. For example, a color-coding system might be used to display pollution data such that, for instance, a green color might indicate an acceptable level of pollutants, a yellow color might indicate a slightly elevated but still acceptable level of pollutants, an orange color might indicate an unacceptable level of pollutants, and a red color might indicate a hazardous level of pollutants.

When a threshold level of an air pollutant is exceeded, for example when an orange or red level is reached, the handset 100 might produce an alarm to alert the user of the handset 100 about the elevated pollution level. The alarm might be a visual signal that appears on the graphical user interface 110, an audible signal that can be heard by the user, and/or a vibration that can be felt by the user.

In an embodiment, the handset 100 is capable of wirelessly transmitting air pollution data collected by the air quality sensor 120. The data might be sent to another handset, a workstation computer, a server computer, or some other receiving device. The receiving device might process the data in several different ways. In one embodiment, the receiving device might be a handset or workstation computer owned by a parent of a child in possession of the handset 100 that transmitted the data. The receiving device might notify the parent that the child has entered a location with an elevated level of air pollution. Upon receiving the notification, the parent might send a message to the child informing the child to vacate the area with the elevated air pollution level. Alternatively, the receiving device might automatically send such a message to the child's handset 100 when the receiving device is notified of the elevated air pollution level.

Figure 2:
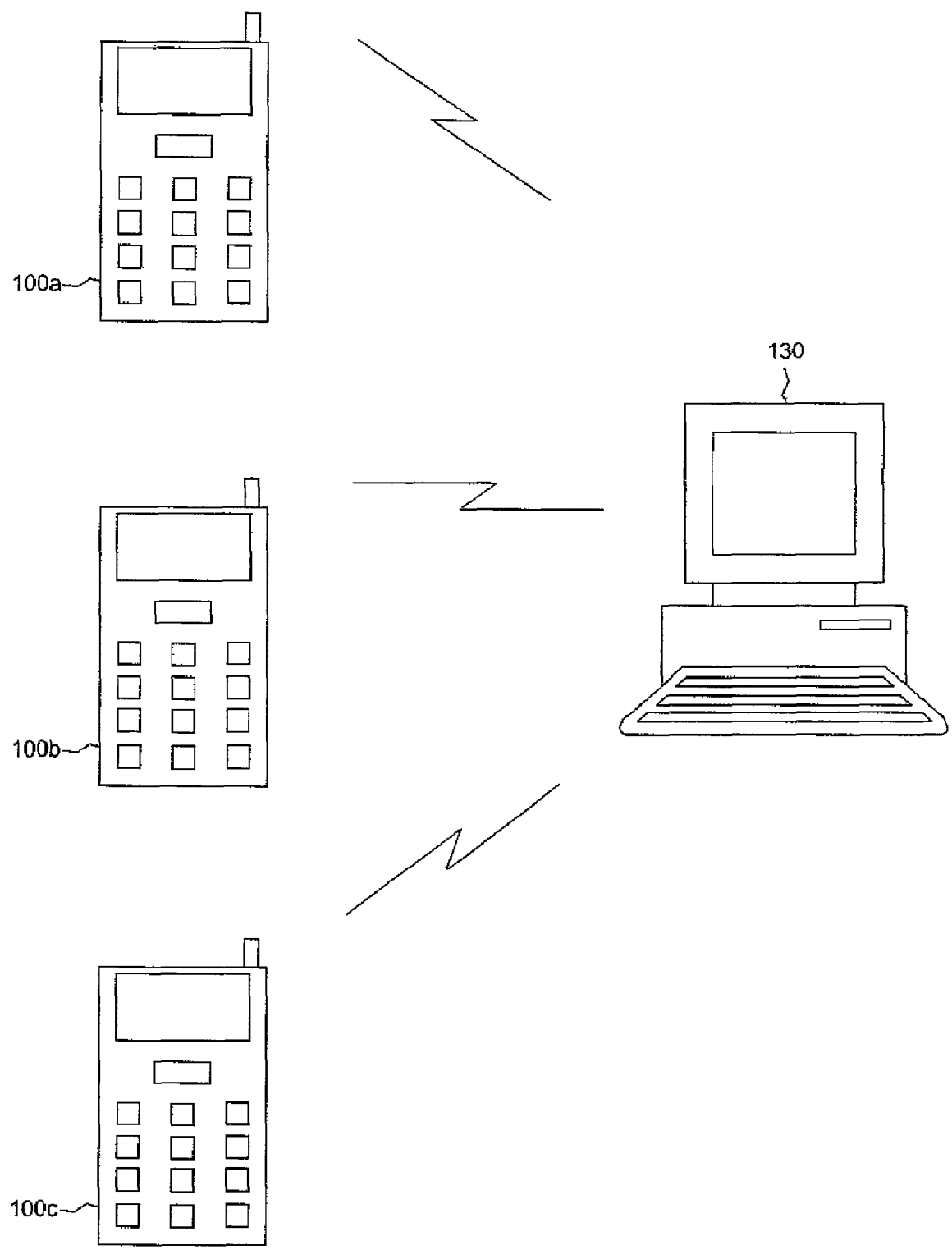
FIG. 2 illustrates a system for recording air pollution levels according to an embodiment of the disclosure.

In another embodiment, a plurality of handsets 100 might send air pollution level measurements to a central server or similar receiving device. This is illustrated in FIG. 2, where a first handset 100a, a second handset 100b, and a third handset 100c transmit data wirelessly to a server 130. While three handsets 100 are shown in FIG. 2, in other embodiments other numbers of handsets 100 could be present. Each of the handsets 100 might be equipped with a global positioning system (GPS) or similar system for determining the location of the handset 100. When one of the handsets 100 sends air pollution level data to the server 130, the handset 100 might also transmit data related to the location, where the air pollution level measurement was obtained. Data might be sent to the server 130 automatically on a periodic basis or might be sent manually by the user of the handset 100.

A wireless telecommunications provider might have many customers, each having such a handset 100. The server 130 might aggregate the data received from the plurality of customers' handsets 100 to create a record of the air pollution levels at multiple locations. When the density of the customers in a particular area is high, the record of the air pollution levels can be much more detailed than a record obtained from a small number of fixed-location air quality monitors spread over a large metropolitan area.

A map might be created showing the air pollution levels measured by the plurality of handsets 100 in the plurality of locations. The map of air pollution levels might be superimposed on a map of a city or other geographical area to create a depiction of the air pollution levels in the area. The map might be updated when new information is received from one of the handsets 100 so that a near real time record is maintained of current air pollution levels in the area. When a large number of air quality measurements are available, the map might be capable of depicting variations in air pollution levels in a relatively small region such as a park or a concert venue.

The server 130 might make the map of air pollution levels available to the plurality of handsets 100 so that a user of one of the handsets 100 can easily determine the air pollution level not only in the user's current location but also in other locations. The user might then make decisions on which areas to enter or not enter based on the air pollution levels in the areas. The server 130 might also publish the map of air pollution levels to the Internet or otherwise make the map of air pollution levels available to subscribers, the public, or other groups.

Handsets 100 equipped with air quality sensors 120 in this manner can allow the creation of air pollution level reports that are more accurate and up-to-date than reports based on data collected by existing fixed-location air pollution monitors. When a large number of handsets 100 transmit air pollution data from a large number of locations within a geographic area, a highly detailed report of the air pollution levels in the area can be generated. Since the report can be updated and re-published or re-broadcast whenever new data is received from one of the handsets 100, a near real time depiction of the air pollution levels in the area can be made available.

Figure 3:
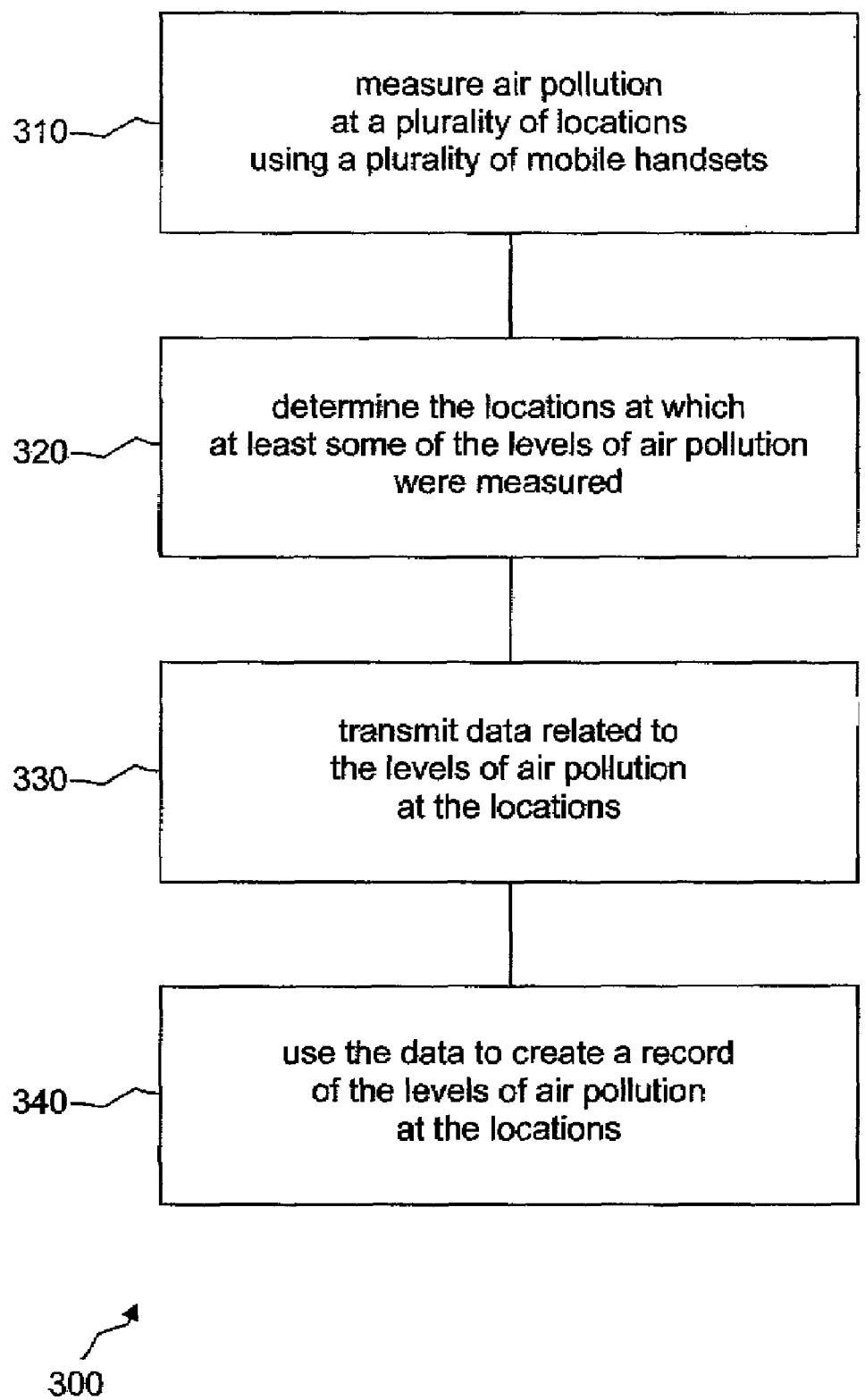
FIG. 3 is a flowchart of a method for measuring air pollution at a plurality of locations according to some of the various embodiments of the present disclosure.

FIG. 3 illustrates method 300 for measuring air pollution at a plurality of locations. In box 310, air pollution levels are measured at a plurality of locations using a plurality of mobile handsets. In box 320, the locations where at least some of the air pollution levels were measured are determined. In box 330, data related to the air pollution levels is transmitted. In box 340, the data is used to create a record of the levels of air pollution at the locations.

Figure 4:
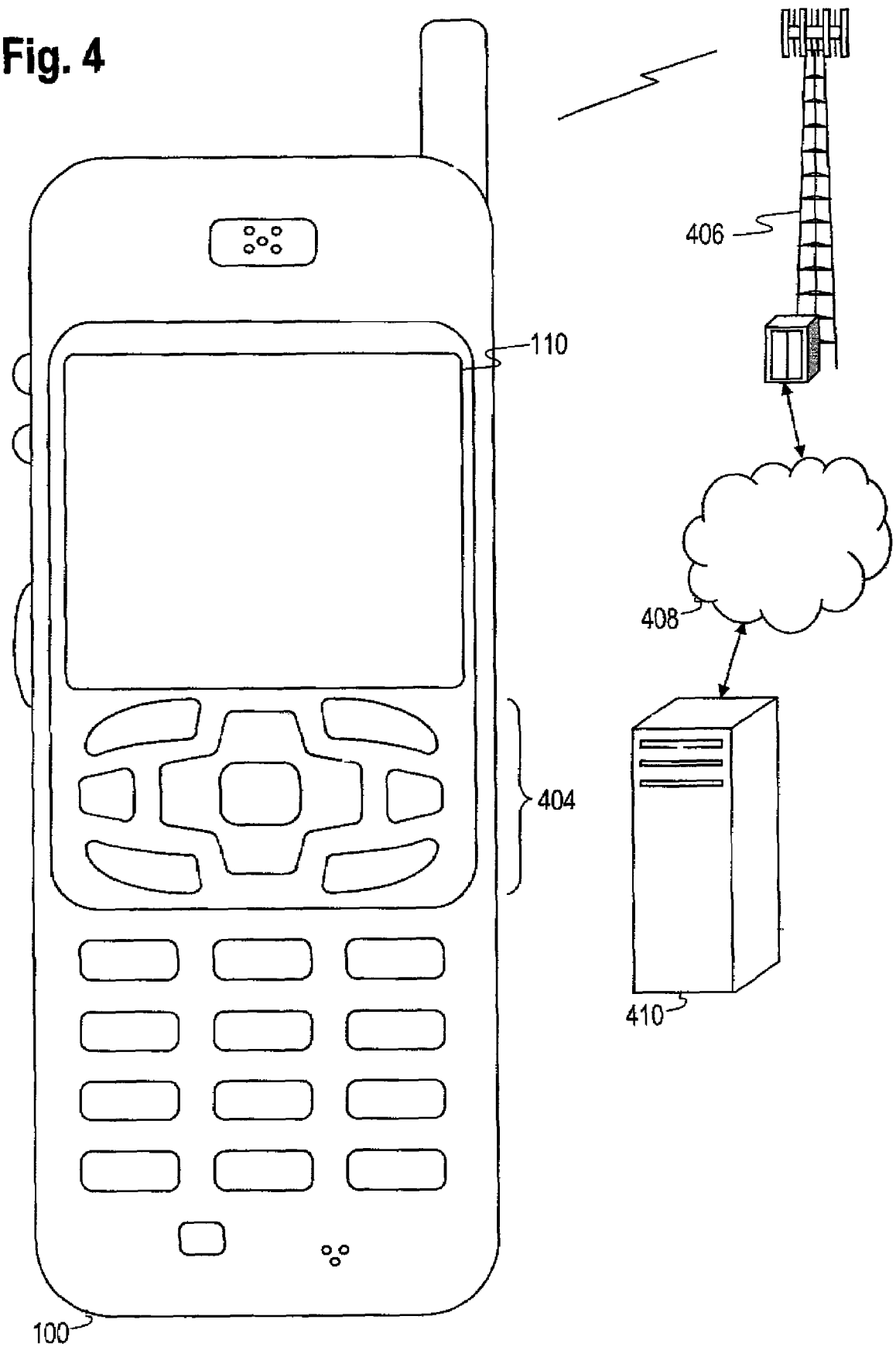
FIG. 4 is a diagram of a wireless communications system including a handset operable for some of the various embodiments of the present disclosure.

FIG. 4 shows a wireless communications system including the handset 100. The handset 100 is operable for implementing aspects of the present disclosure, but the present disclosure should not be limited to these implementations. Though illustrated as a mobile phone, the handset 100 may take various forms including a wireless handset, a pager, a personal digital assistant (PDA), a portable computer, a tablet computer, or a laptop computer. Many suitable handsets combine some or all of these functions. In some embodiments of the present disclosure, the handset 100 is not a general purpose computing device like a portable, laptop or tablet computer, but rather is a special-purpose communications device such as a mobile phone, wireless handset, pager, or PDA.

The handset 100 includes a display 110 and a touch-sensitive surface or keys 404 for input by a user. The handset 100 may present options for the user to select, controls for the user to actuate, and/or cursors or other indicators for the user to direct. The handset 100 may further accept data entry from the user, including numbers to dial or various parameter values for configuring the operation of the handset 100. The handset 100 may further execute one or more software or firmware applications in response to user commands. These applications may configure the handset 100 to perform various customized functions in response to user interaction.

Among the various applications executable by the handset 100 are a web browser, which enables the display 110 to show a web page. The web page is obtained via wireless communications with a cell tower 406, a wireless network access node, or any other wireless communication network or system. The cell tower 406 (or wireless network access node) is coupled to a wired network 408, such as the Internet. Via the wireless link and the wired network, the handset 100 has access to information on various servers, such as a server 410. The server 410 may provide content that may be shown on the display 110. The server 410 of FIG. 4 may or may not be the same as the server 130 of FIG. 2.

FIG. 5 shows a block diagram of the handset 100. The handset 100 includes a digital signal processor (DSP) 502 and a memory 504. As shown, the handset 100 may further include an antenna and front end unit 506, a radio frequency (RF) transceiver 508, an analog baseband processing unit 510, a microphone 512, an earpiece speaker 514, a headset port 516, an input/output interface 518, a removable memory card 520, a universal serial bus (USB) port 522, an infrared port 524, a vibrator 526, a keypad 528, a touch screen liquid crystal display (LCD) with a touch sensitive surface 530, a touch screen/LCD controller 532, a charge-coupled device (CCD) camera 534, a camera controller 536, and a global positioning system (GPS) sensor 538.

The DSP 502 or some other form of controller or central processing unit operates to control the various components of the handset 100 in accordance with embedded software or firmware stored in memory 504. In addition to the embedded software or firmware, the DSP 502 may execute other applications stored in the memory 504 or made available via information carrier media such as portable data storage media like the removable memory card 520 or via wired or wireless network communications. The application software may comprise a compiled set of machine-readable instructions that configure the DSP 502 to provide the desired functionality, or the application software may be high-level software instructions to be processed by an interpreter or compiler to indirectly configure the DSP 502.

The antenna and front end unit 506 may be provided to convert between wireless signals and electrical signals, enabling the handset 100 to send and receive information from a cellular network or some other available wireless communications network. The RF transceiver 508 provides frequency shifting, converting received RF signals to baseband and converting baseband transmit signals to RF. The analog baseband processing unit 510 may provide channel equalization and signal demodulation to extract information from received signals, may modulate information to create transmit signals, and may provide analog filtering for audio signals. To that end, the analog baseband processing unit 510 may have ports for connecting to the built-in microphone 512 and the earpiece speaker 514 that enable the handset 100 to be used as a cell phone. The analog baseband processing unit 510 may further include a port for connecting to a headset or other hands-free microphone and speaker configuration.

The DSP 502 may send and receive digital communications with a wireless network via the analog baseband processing unit 510. In some embodiments, these digital communications may provide Internet connectivity, enabling a user to gain access to content on the Internet and to send and receive email or text messages. The input/output interface 518 interconnects the DSP 502 and various memories and interfaces. The memory 504 and the removable memory card 520 may provide software and data to configure the operation of the DSP 502. Among the interfaces may be the USB interface 522 and the infrared port 524. The USB interface 522 may enable the handset 100 to function as a peripheral device to exchange information with a personal computer or other computer system. The infrared port 524 and other optional ports such as a Bluetooth interface or an IEEE 802.11 compliant wireless interface may enable the handset 100 to communicate wirelessly with other nearby handsets and/or wireless base stations.

The input/output interface 518 may further connect the DSP 502 to the vibrator 526 that, when triggered, causes the handset 100 to vibrate. The vibrator 526 may serve as a mechanism for silently alerting the user to any of various events such as an incoming call, a new text message, an appointment reminder, and an elevated air pollution level.

The keypad 528 couples to the DSP 502 via the interface 518 to provide one mechanism for the user to make selections, enter information, and otherwise provide input to the handset 100. Another input mechanism may be the touch screen LCD 530, which may also display text and/or graphics to the user. The touch screen LCD controller 532 couples the DSP 502 to the touch screen LCD 530.

The CCD camera 534 enables the handset 100 to take digital pictures. The DSP 502 communicates with the CCD camera 534 via the camera controller 536. The GPS sensor 538 is coupled to the DSP 502 to decode global positioning system signals, thereby enabling the handset 100 to determine its position. Various other peripherals may also be included to provide additional functions, e.g., radio and television reception.

FIG. 6 illustrates a software environment 602 that may be implemented by the DSP 502. The DSP 502 executes operating system drivers 604 that provide a platform from which the rest of the software operates. The operating system drivers 604 provide drivers for the handset hardware with standardized interfaces that are accessible to application software. The operating system drivers 604 include application management services ("AMS") 606 that transfer control between applications running on the handset 100. Also shown in FIG. 6 are a web browser application 608, a media player application 610, and Java applets 612. The web browser application 608 configures the handset 100 to operate as a web browser, allowing a user to enter information into forms and select links to retrieve and view web pages. The media player application 610 configures the handset 100 to retrieve and play audio or audiovisual media. The Java applets 612 configure the handset 100 to provide games, utilities, and other functionality. Air quality-related software 614 might receive and process data received from the air quality sensor 120.

Figure 7:
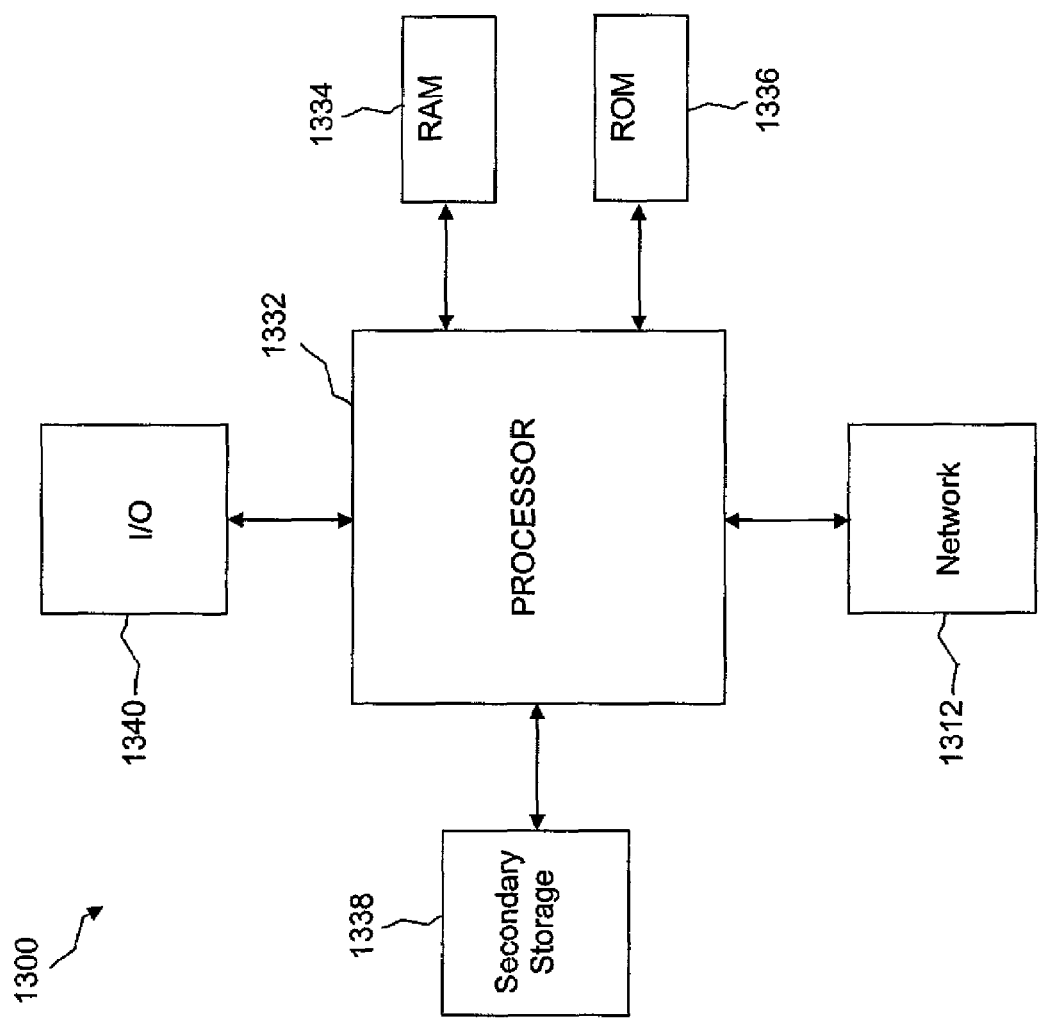
FIG. 7 is a diagram of typical, general-purpose computer system suitable for implementing one or more embodiments disclosed herein.

The servers 130 and 410 described above may be implemented on any general-purpose computer with sufficient processing power, memory resources, and network throughput capability to handle the necessary workload placed upon it. FIG. 7 illustrates a typical, general-purpose computer system 1300 suitable for implementing one or more embodiments disclosed herein, including operating as the server 130 and/or the server 410. The computer system 1300 includes a processor 1332 (which may be referred to as a central processor unit or CPU) that is in communication with memory devices including secondary storage 1338, read only memory (ROM) 1336, random access memory (RAM) 1334, input/output (I/O) devices 1340, and network connectivity devices 1312. The processor 1332 may be implemented as one or more CPU chips.

The secondary storage 1338 is typically comprised of one or more disk drives or tape drives and is used for non-volatile storage of data and as an overflow data storage device if the RAM 1334 is not large enough to hold all working data. Secondary storage 1338 may be used to store programs which are loaded into the RAM 1334 when such programs are selected for execution. The ROM 1336 is used to store instructions and perhaps data which are read during program execution. The ROM 1336 is a non-volatile memory device which typically has a small memory capacity relative to the larger memory capacity of the secondary storage 1338. The RAM 1334 is used to store volatile data and perhaps to store instructions. Access to both ROM 1336 and RAM 1334 is typically faster than to secondary storage 1338.

I/O devices 1340 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 1312 may take the form of modems, modem banks, ethernet cards, universal serial bus (USB) interface cards, serial interfaces, token ring cards, fiber distributed data interface (FDDI) cards, wireless local area network (WLAN) cards, ultra-wideband (UWB) cards, radio transceiver cards such as code division multiple access (CDMA) and/or global system for mobile communications (GSM) radio transceiver cards, and other well-known network devices. These network connectivity devices 1312 may enable the processor 1332 to communicate with the Internet or one or more intranets. With such a network connection, it is contemplated that the processor 1332 might receive information from the network, or might output information to the network in the course of performing the above-described method steps. Such information, which is often represented as a sequence of instructions to be executed using the processor 1332, may be received from and outputted to the network, for example, in the form of a computer data signal embodied in a carrier wave.

Such information, which may include data or instructions to be executed using the processor 1332 for example, may be received from and outputted to the network, for example, in the form of a computer data baseband signal or signal embodied in a carrier wave. The baseband signal or signal embodied in the carrier wave generated by the network connectivity devices 1312 may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art.

The processor 1332 executes instructions, codes, computer programs, and scripts which it accesses from hard disk, floppy disk, optical disk (these various disk-based systems may all be considered secondary storage 1338), ROM 1336, RAM 1334, or the network connectivity devices 1312.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as directly coupled or communicating with each other may be coupled through some interface or device, such that the items may no longer be considered directly coupled to each other but may still be indirectly coupled and in communication, whether electrically, mechanically, or otherwise with one another. Other examples of changes, substitutions, and alterations are ascertainable by one skilled in the art and could be made without departing from the spirit and scope disclosed herein.

What is claimed is:

1. A mobile telecommunications handset, comprising:
   a component configured to measure a level of an air pollutant;
   a transceiver configured to send and receive communications wirelessly, the communications comprising data related to the measurements of the air pollutant;
   a system configured to determine a location of the mobile telecommunications handset; and
   a display configured to display data related to the measurements of the air pollutant generated from one or more other handsets, wherein the display is configured to superimpose at least one map and a location associated with at least some of the measurements of the air pollutant.

2. The handset of claim 1, wherein the data comprises numerical data related to the level of the air pollutant.

3. The handset of claim 1, wherein the data comprises graphical data related to the level of the air pollutant.

4. The handset of claim 1, further comprising an alarm operable to be activated when the level of the air pollutant exceeds a threshold to alert the user of the mobile telecommunications handset.

5. The handset of claim 1, wherein the handset is operable to wirelessly transmit data related to the level of the air pollutant to another device.

6. The handset of claim 5, wherein the handset is operable to receive a notification from the other device regarding the level of the air pollutant.

7. The handset of claim 1, wherein the transceiver is configured to transmit the data related to the measurements of the air pollutant to a server, the server configured to:
   receive a plurality location information and pollutant data from a plurality of handsets, the pollutant data comprising a level of the air pollutant measured by each of the plurality of handsets;
   determine a location for each of the plurality of handsets;
   aggregate the pollutant data received from the plurality of handsets and the locations for each the plurality of handsets; and create a record of air pollutant levels corresponding to the locations for each of the plurality of handsets.

8. The handset of claim 7, wherein the mobile telecommunications handset is further operable to receive from the server the record of the air pollutant levels.

9. A system for recording a plurality of levels of an air pollutant at a plurality of locations comprising:
a plurality of handsets operable to measure the plurality of levels of the air pollutant;
a component operable to promote determining a plurality of locations corresponding to respective ones of the plurality of handsets, the plurality of handsets operable to transmit and receive the data related to the levels of the air pollutant and the locations;
a receiving device operable to receive the data related to the levels of the air pollutant and the locations and use the data to create a record of the levels of the air pollutant at the plurality of locations;
wherein at least one of the plurality of handsets are configured to receive the data related to the measurements of the air pollutant; and
a display on the at least one handset, the display configured to display the data related to the measurements of the air pollutant generated from one or more other of the plurality of handsets, wherein the display superimposes at least one map and a location associated with at least some of the measurements of the air pollutant.

10. The system of claim 9, wherein the air pollutants measured include at least one of:
carbon monoxide; and
ozone.

11. The system of claim 9, wherein the component operable to promote determining the locations is further defined as at least one of:
a global positioning system; and
a triangulation component.

12. The system of claim 9, wherein the data related to the measurements of pollutants comprises at least one of numerical data and graphical data related to at least one of the levels of the air pollutant.

13. The system of claim 9, wherein at least one of the handsets includes an alarm operable to be activated when at least one of the levels of the air pollutant exceeds a threshold.

14. The system of claim 12, wherein each of the plurality of handsets comprises:
a transceiver operable for a user to communicate wirelessly;
a display; and
a keypad.

15. A method for measuring air pollution at a plurality of locations comprising:
receiving air pollution measurement data from a plurality of mobile handsets;
determining locations at which at least some levels of air pollution were measured;
using the air pollution measurement data to create a record of levels of air pollution at the locations;
transmitting at least a portion of the data to at least one of the plurality of handsets;
displaying, on the at least one handset, the data related to the measurements of the air pollutant generated from one or more other of the plurality of handsets, wherein the display superimposes at least one map and a location associated with at least some of the measurements of the air pollutant.

16. The method of claim 15, wherein the measuring of the levels of air pollution is performed by air quality sensors on the plurality of mobile handsets.

17. The method of claim 16, wherein transmitting the at least a portion of the record comprises transmitting a record of the levels of air pollution in a geographic region prior to the at least one mobile handset entering into the geographic region.

18. The method of claim 16, further comprising making the record of the levels of air pollution at the locations available to other devices other than the plurality of mobile handsets.

19. The method of claim 16, further comprising:
setting an alarm related to a first mobile handset to activate when the level of air pollution adjacent the location of the first mobile handset exceeds a threshold; and
transmitting a notice to a second mobile handset when the alarm set for the first mobile handset is activated.

20. The method of claim 16, further comprising setting an alarm on one of the mobile handsets and activating the alarm when the level of air pollution exceeds a threshold.

* * * * *